US012796995B2

(12) United States Patent
Tsuyuki

(10) Patent No.: US 12,796,995 B2
(45) Date of Patent: Nov. 17, 2026

(54) MEDICAL IMAGE DIAGNOSIS APPARATUS, X-RAY COMPUTED TOMOGRAPHY APPARATUS, AND MEDICAL IMAGE DIAGNOSIS SYSTEM

(71) Applicant: Canon Kabushiki Kaisha, Tokyo (JP)

(72) Inventor: Masaharu Tsuyuki, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 18/814,659

(22) Filed: Aug. 26, 2024

(65) Prior Publication Data

US 2025/0072809 A1 Mar. 6, 2025

(30) Foreign Application Priority Data

Aug. 28, 2023 (JP) ................................ 2023-138375

(51) Int. Cl.
*A61B 5/318* (2021.01)
*A61B 5/00* (2006.01)
*A61B 6/00* (2024.01)
*A61B 6/03* (2006.01)

(52) U.S. Cl.
CPC ............ *A61B 5/318* (2021.01); *A61B 5/0064* (2013.01); *A61B 6/032* (2013.01); *A61B 6/4447* (2013.01)

(58) Field of Classification Search
CPC ....... A61B 5/318; A61B 5/0064; A61B 6/032; A61B 6/4447; A61B 5/352; A61B 5/7292; A61B 6/503; A61B 6/541
See application file for complete search history.

(56) References Cited

U.S. PATENT DOCUMENTS 6,226,350 B1 * 5/2001 Hsieh ..................... A61B 6/032 378/98.2
2008/0187092 A1 * 8/2008 Boese .................... A61B 6/541 378/8
2009/0060120 A1 * 3/2009 Mukumoto ............ A61B 6/503 378/8
2015/0182173 A1 * 7/2015 Yang .................... G01R 33/546 600/407
2017/0086771 A1 * 3/2017 Yasuhiro ................ G16H 50/30

FOREIGN PATENT DOCUMENTS

JP 2001-276061 A 10/2001

OTHER PUBLICATIONS

Sano T, Kondo T, Matsutani H, Morita H, Arai T, Sekine T, Takase S, Oida A, Fukazawa H, Kodama T, Kondo M, Orihara T, Yamada N, Narula J. Significance of PQ interval in acquisition of coronary multidetector row computed tomography. J Cardiol. Dec. 2009 (Year: 2009).*
Matsumoto H, Kondo T, Watanabe S, Kikumoto R, Shimada T, Hiraoka Y, Ueda K. ECG-edited middiastolic phase reconstruction improves image quality at 64-MDCT coronary angiography of patients with atrial fibrillation. AJR Am J Roentgenol. 2008 (Year: 2012).*

* cited by examiner

*Primary Examiner* — Pascal M Bui Pho
*Assistant Examiner* — Nicholas A Robinson
(74) *Attorney, Agent, or Firm* — Oblon, McClelland, Maier & Neustadt, L.L.P.

(57) ABSTRACT

A medical image diagnosis apparatus according to an embodiment includes processing circuitry. The processing circuitry obtains biological information as to a subject acquired by a biological monitor, obtains analysis information resulting from analysis of the biological information, and sets an examination condition for capturing an image of (Continued)

351

| DIAGNOSIS INFORMATION | EXAMINATION CONDITION | |
|---|---|---|
| | SCAN CONDITION | RECONSTRUCT CONDITION |
| EQUAL PULSE (NORMAL SINUS RHYTHM) AND HEART RATE OF 65 bpm OR LESS | IRRADIATE ONLY IN MIDDIASTOLE | RECONSTRUCT MIDDIASTOLE |
| ATRIOVENTRICULAR BLOCK | CORRECT HR THRESHOLD ACCORDING TO PR INTERVAL<br>AIM FOR MIDDIASTOLE BUT MOVE UP IRRADIATION PERIOD ACCORDING TO PR INTERVAL | RECONSTRUCT IMMEDIATELY PRIOR TO P WAVE BASED ON PR-INTERVAL INFORMATION |
| ATRIAL FIBRILLATION | PREPARE FREE AREA FOR DATA ACQUISITION FOR SEVERAL SECONDS<br>START IRRADIATION FROM R WAVE+450 ms<br>END IRRADIATION AT NEXT R WAVE<br>END DATA ACQUISITION WHEN 250 ms DATA IS OBTAINED FROM R WAVE+450 ms | RECONSTRUCT REAR END OF 250 ms DATA |
| VENTRICULAR PREMATURE CONTRACTION | PREPARE LARGER FREE AREA FOR EXTENSION OF DATA ACQUISITION DUE TO IRREGULAR PULSE<br>END DATA ACQUISITION WHEN EQUAL PULSE OR LONGER RR IS OBTAINED | RECONSTRUCT EQUAL PULSE OR MIDDIASTOLE OF LONGER RR |
| VENTRICULAR PREMATURE CONTRACTION (BIGEMINY) | PERFORM SCAN, AIMING FOR SECOND HALF OF LONGER RR | RECONSTRUCT SECOND HALF OF LONGER RR |

the subject by a scan, based on the biological information and the analysis information.

5 Claims, 7 Drawing Sheets

FIG.2

351

| DIAGNOSIS INFORMATION | EXAMINATION CONDITION | |
|---|---|---|
| | SCAN CONDITION | RECONSTRUCT CONDITION |
| EQUAL PULSE (NORMAL SINUS RHYTHM) AND HEART RATE OF 65 bpm OR LESS | IRRADIATE ONLY IN MIDDIASTOLE | RECONSTRUCT MIDDIASTOLE |
| ATRIOVENTRICULAR BLOCK | CORRECT HR THRESHOLD ACCORDING TO PR INTERVAL<br>AIM FOR MIDDIASTOLE BUT MOVE UP IRRADIATION PERIOD ACCORDING TO PR INTERVAL | RECONSTRUCT IMMEDIATELY PRIOR TO P WAVE BASED ON PR-INTERVAL INFORMATION |
| ATRIAL FIBRILLATION | PREPARE FREE AREA FOR DATA ACQUISITION FOR SEVERAL SECONDS<br>START IRRADIATION FROM R WAVE+450 ms<br>END IRRADIATION AT NEXT R WAVE<br>END DATA ACQUISITION WHEN 250 ms DATA IS OBTAINED FROM R WAVE+450 ms | RECONSTRUCT REAR END OF 250 ms DATA |
| VENTRICULAR PREMATURE CONTRACTION | PREPARE LARGER FREE AREA FOR EXTENSION OF DATA ACQUISITION DUE TO IRREGULAR PULSE<br>END DATA ACQUISITION WHEN EQUAL PULSE OR LONGER RR IS OBTAINED | RECONSTRUCT EQUAL PULSE OR MIDDIASTOLE OF LONGER RR |
| VENTRICULAR PREMATURE CONTRACTION (BIGEMINY) | PERFORM SCAN, AIMING FOR SECOND HALF OF LONGER RR | RECONSTRUCT SECOND HALF OF LONGER RR |

MEDICAL IMAGE DIAGNOSIS APPARATUS, X-RAY COMPUTED TOMOGRAPHY APPARATUS, AND MEDICAL IMAGE DIAGNOSIS SYSTEM

CROSS-REFERENCE TO RELATED APPLICATION

This application is based upon and claims the benefit of priority from Japanese Patent Application No. 2023-138375, filed on Aug. 28, 2023; the entire contents of which are incorporated herein by reference.

FIELD

Embodiments described herein relate generally to a medical image diagnosis apparatus, an X-ray computed tomography apparatus, and a medical image diagnosis system.

BACKGROUND

For examination purposes, medical image diagnosis apparatuses such as an X-ray computed tomography (CT) apparatus are used to generate medical images. Affected by organ motion as cardiac motion, for example, such medical images may include artifacts. To eliminate the influences of cardiac motion, for example, the X-ray CT apparatus performs retrospective ECG-gated image reconstruction. The retrospective ECG-gated image reconstruction is a technique to acquire projection data and measure electrocardiogram waveforms of a subject at the same time to acquire image data based on the electrocardiogram waveforms for reconstruction of CT images.

BRIEF DESCRIPTION OF THE DRAWINGS

FIG. 2 illustrates a data configuration of an examination-condition database (DB) according to an embodiment, as an example;

DETAILED DESCRIPTION

According to an embodiment, a medical image diagnosis apparatus includes processing circuitry. The processing circuitry obtains biological information as to a subject acquired by a biological monitor; obtain analysis information resulting from analysis of the biological information; and set an examination condition for capturing an image of the subject by a scan, based on the biological information and the analysis information.

Hereinafter, embodiments of an X-ray computed tomography (CT) apparatus will be described in detail with reference to the accompanying drawings. The X-ray CT apparatus is one example of medical image diagnosis apparatus.

Figure 1:
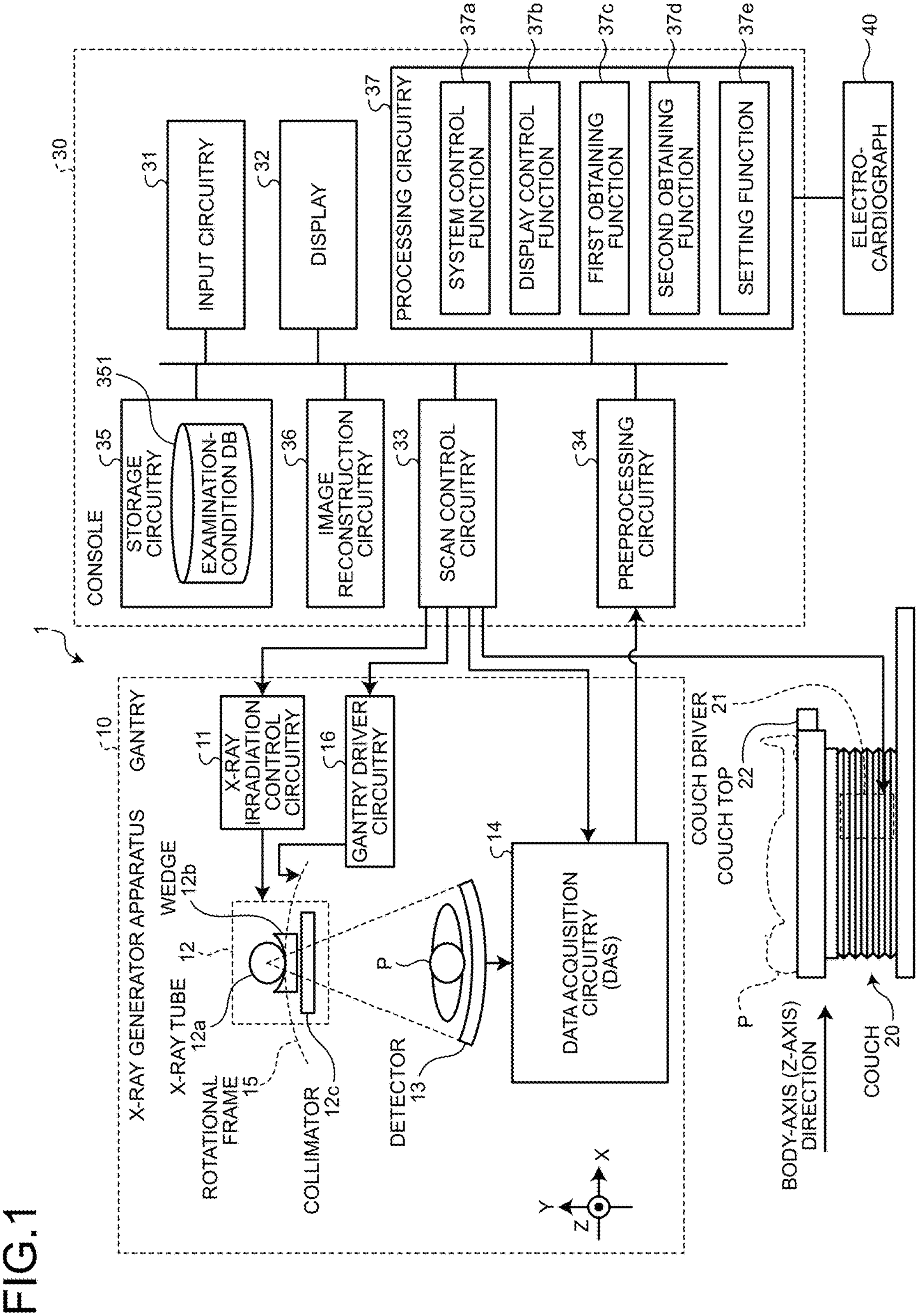
FIG. 1 illustrates an exemplary configuration of an X-ray CT apparatus according to an embodiment.

FIG. 1 is a schematic diagram illustrating an exemplary configuration of an X-ray CT apparatus 1 according to an embodiment. As illustrated in FIG. 1, the X-ray CT apparatus 1 of an embodiment includes a gantry 10, a couch 20, and a console 30. The X-ray CT apparatus 1 is connected to an electrocardiograph 40 as illustrated in FIG. 1. A system including the X-ray CT apparatus 1 and the electrocardiograph 40 is one example of medical image diagnosis system.

The gantry 10 serves to irradiate a subject P (patient) with X-rays to detect the X-rays having transmitted the subject P for output to the console 30. The gantry 10 includes X-ray irradiation control circuitry 11, an X-ray generator apparatus 12, a detector 13, data acquisition circuitry (data acquisition system: DAS) 14, a rotational frame 15, and gantry driver circuitry 16.

In the gantry 10 of FIG. 1, an orthogonal coordinate system of X-axis, Y-axis, and Z-axis is defined. Specifically, the X-axis indicates a horizontal direction, the Y-axis indicates a vertical direction, and the Z-axis indicates a rotational axis direction of the rotational frame 15 in a non-tilt state of the gantry 10.

The rotational frame 15 is an annular frame that supports the X-ray generator apparatus 12 and the X-ray detector 13 in opposing positions across the subject P to rotate at high speed on a circular path around the subject P under the control of the gantry driver circuitry 16 as described later.

The X-ray irradiation control circuitry 11 serves as a high-voltage generator that supplies a high voltage to an X-ray tube 12*a*. The X-ray tube 12*a* generates X-rays using the high voltage supplied from the X-ray irradiation control circuitry 11. Under the control of later-described scan control circuitry 33, the X-ray irradiation control circuitry 11 regulates an amount of X-rays to irradiate the subject P by regulating a supply of tube voltage and tube current to the X-ray tube 12*a*.

The X-ray irradiation control circuitry 11 also performs switching of wedges 12*b*. In addition the X-ray irradiation control circuitry 11 adjusts the X-ray irradiation range (fan angle or cone angle) by adjusting the aperture of a collimator 12*c*. In the present embodiment, the operator may manually switch multiple kinds of wedges.

The X-ray generator apparatus 12 includes the X-ray tube 12*a*, the wedges 12*b*, and the collimator 12*c*, to generate X-rays for irradiating the subject P.

The X-ray tube 12*a* is a vacuum tube to be applied with a high voltage from a not-shown high-voltage generator to irradiate the subject P with X-ray beams. Along with the rotation of the rotational frame 15, the X-ray tube 12*a* emits X-ray beams to the subject P. The X-ray tube 12*a* generates X-ray beams to diverge at a fan angle and a cone angle.

For example, under the control of the X-ray irradiation control circuitry 11, the X-ray tube 12*a* is able to successively emit X-rays to the entire perimeter of the subject P for full reconstruction and successively emit X-rays in a half-reconstructible irradiation range (180 degrees+fan angle) for half reconstruction. Under the control of the X-ray irradiation control circuitry 11, the X-ray tube 12*a* is also able to intermittently emit X-rays (pulsed X-rays) at a preset position (tube position).

The X-ray irradiation control circuitry 11 can modify the intensity of X-rays to be emitted from the X-ray tube 12*a*. For example, the X-ray irradiation control circuitry 11 increases the X-ray emission of the X-ray tube 12*a* in intensity at a particular tube position and decreases the X-ray emission of the X-ray tube 12*a* in intensity in a range outside the particular tube position.

The wedges 12*b* serve as X-ray filters that regulate an amount of X-rays emitted from the X-ray tube 12*a*.

Specifically, the wedges 12*b* are filters to allow the X-rays emitted from the X-ray tube 12*a* to transmit therethrough for attenuation, so that the subject P is irradiated with the X-rays from the X-ray tube 12*a* in a predefined distribution. The wedges 12*b* are formed of aluminum to have a given target angle and a given thickness, for instance. The wedge may be referred to as a wedge filter or a bow-tie filter.

The collimator 12*c* is slits for restricting the irradiation range of the X-rays after adjusted in amount by the wedges 12*b* under the control of the X-ray irradiation control circuitry 11.

The gantry driver circuitry 16 rotates the X-ray generator apparatus 12 and the detector 13 on the circular path around the subject P by rotating the rotational frame 15.

The detector 13 is a two-dimensional array detector (area detector) that detects the X-rays having transmitted the subject P. The detector 13 includes, for example, multiple arrays of X-ray detector elements for multiple channels arranged along the body axis (in the Z-axis direction in FIG. 1) of the subject P.

Specifically, in the present embodiment the detector 13 includes a large number of X-ray detector element arrays, e.g., 320 arrays, in the body-axis direction of the subject P. The detector 13 is capable of detecting the X-rays having transmitted a large area of the subject P, e.g., an area including the lungs or the heart of the subject P.

The data acquisition circuitry 14 is a DAS that acquires projection data from detection data on the X-rays detected by the detector 13.

For example, the data acquisition circuitry 14 subjects X-ray-intensity distribution data detected by the detector 13 to amplification, A/D conversion, and sensitivity correction among the channels, to generate projection data and transmit the resultant projection data to the console 30. As an example, with respect to the X-rays successively emitted from the X-ray tube 12*a* during the rotation of the rotational frame 15, the data acquisition circuitry 14 acquires projection datasets corresponding to the entire perimeter (by 360 degrees).

The data acquisition circuitry 14 also transmits to the console 30 the projection datasets and the tube positions in association with each other. The tube positions serve as information representing the projection direction of the projection data. Preprocessing circuitry 34 as described later may perform sensitivity correction among the channels.

The couch 20 is an apparatus on which the subject P is to lie. As illustrated in FIG. 1, the couch 20 includes a couch driver 21 and a couch top 22. The couch driver 21 drives the couch top 22 in the Z-axis direction to move the subject P into the rotational frame 15. The couch top 22 is a plate on which the subject P is to be laid.

The gantry 10 performs, for example, a helical scan, i.e., scanning the subject P in a helical manner by rotating the rotational frame 15 while moving the couch top 22. Also, the gantry 10 performs a conventional scan i.e., scanning the subject P in a stationary position on the circular path by rotating the rotational frame 15 after moving the couch top 22. Further, the gantry 10 performs a step and shoot scan, i.e., performing a conventional scan in multiple scan areas while moving the couch top 22 in position with constant intervals.

The console 30 serves to allow an operator to manipulate the X-ray CT apparatus 1, and reconstruct X-ray CT image data based on the projection data acquired by the gantry 10. As illustrated in FIG. 1, the console 30 includes input circuitry 31, a display 32, the scan control circuitry 33, the preprocessing circuitry 34, storage circuitry 35, image reconstruction circuitry 36, and processing circuitry 37.

The input circuitry 31 includes various elements, such as a mouse, a keyboard, a trackball, a switch, a button, and a joystick, with which the operator of the X-ray CT apparatus 1 inputs various kinds of instructions and settings. The input circuitry 31 transfers information representing the operator's instructions and settings to the processing circuitry 37.

For example, the input circuitry 31 receives an operator's input to select an examination for the subject P. The input circuitry 31 also receives a designation of a region on the image. In addition the input circuitry 31 may receive a scan condition for X-ray CT image data, a reconstruction condition for reconstructing X-ray CT image data, and an image processing condition for X-ray CT image data from the operator.

The display 32 serves as a monitor which the operator views. Under the control of the processing circuitry 37, the display 32 displays image data generated from the X-ray CT image data for the operator and a graphical user interface (GUI) that allows the operator to input various kinds of instructions and settings via the input circuitry 31.

Under the control of the processing circuitry 37, the scan control circuitry 33 controls the operations of the X-ray irradiation control circuitry 11, the gantry driver circuitry 16, the data acquisition circuitry 14, and the couch driver 21 to cause the gantry 10 to perform projection-data acquisition. Specifically, according to the scan condition set by the processing circuitry 37, the scan control circuitry 33 individually controls scanning for acquiring localizer radiographs (scanograms) and projection-data acquisition in main scanning to acquire images for use in diagnosis. Determination as to the scan condition by the processing circuitry 37 will be described below. In the present embodiment the X-ray CT apparatus 1 is capable of capturing two-dimensional and three-dimensional scanograms.

For example, the scan control circuitry 33 captures a two-dimensional scanogram of the subject P by consecutively scanning the subject P while moving the couch top 22 at constant speed, with the X-ray tube 12*a* remaining stationary at 0-degree position (frontward position relative to the subject P).

Alternatively, the scan control circuitry 33 captures a two-dimensional scanogram of the subject P by iteratively scanning the subject P in synchronization with intermittent movements of the couch top 22 while the X-ray tube 12*a* remains stationary at 0-degree position. The scan control circuitry 33 can capture a localizer radiograph of the subject P from an optional direction (e.g., lateral direction), in addition to the frontward direction.

Further, the scan control circuitry 33 can capture a three-dimensional scanogram of the subject P by acquiring the projection data of the entire perimeter of the subject P. For example, the scan control circuitry 33 can acquire the projection data of the entire perimeter of the subject P by a helical scan or non-helical scan.

The scan control circuitry 33 can perform a helical scan or a non-helical scan of a large area of the subject P, such as the entire chest region, the entire abdominal region, the whole upper body, and the whole body, at a lower dose than that of a main scan. Examples of the non-helical scan includes step and shoot scanning as described above.

As such, the scan control circuitry 33 can acquire the projection data of the entire perimeter of the subject P. This enables the image reconstruction circuitry 36 to reconstruct three-dimensional X-ray CT image data (volume data) and generate a localizer image based on the reconstructed volume data from an optional direction, as described below.

Dimension of localizer images to be captured, i.e., two-dimension or three-dimension may be set freely by the operator or set in advance depending on the items of an examination.

The preprocessing circuitry 34 subjects the projection data generated by the data acquisition circuitry 14 to correction processing including, for example, logarithm conversion, offset correction, sensitivity correction, and beam hardening correction, to generate corrected projection data.

Specifically, the preprocessing circuitry 34 generates corrected projection data of projection data of the localizer image generated by the data acquisition circuitry 14 and of projection data acquired by the main scan, and stores the corrected projection data in the storage circuitry 35.

The storage circuitry 35 stores therein various kinds of information, for example, the projection data generated by the preprocessing circuitry 34. Specifically, the storage circuitry 35 stores projection data of localizer images generated by the preprocessing circuitry 34 and projection data acquired for diagnosis purpose by the main scan.

The storage circuitry 35 further stores an examination-condition database (DB) 351. The examination-condition database 351 contains data for determining an examination condition of an X-ray CT examination. The examination condition refers to, for example, a scan condition and a reconstruction condition for obtaining an image of the subject by a scan. With reference to FIG. 2, an example of data configuration of the examination-condition database 351 will be explained below. FIG. 2 depicts an exemplary data configuration of the examination-condition database 351.

In FIG. 2 the examination-condition database 351 stores diagnosis information and examination conditions in association with each other. In FIG. 2 the diagnosis information represents electrocardiographic findings obtained by analyzing electrocardiogram waveforms output from the electrocardiograph 40. The means to analyze electrocardiogram waveforms is not limited to a particular one and any of a variety of known analyzing techniques is adoptable. In FIG. 2 the examination condition refers to information representing a scan condition and a reconstruction condition for X-ray CT examination.

In FIG. 2 the scan condition refers to information defining the operations of the gantry 10 and the couch driver 21 and X-ray irradiation timing, for example. In FIG. 2 the reconstruction condition refers to information defining the timing of X-ray CT image data obtained to be reconstructed.

As an example, the first row of the database in FIG. 2 represents that when the diagnosis information indicates "equal pulse (normal sinus rhythm) and heart rate of 65 bpm or less", the scan condition of the examination condition is "irradiation only during middiastole" and the reconstruction condition is "reconstruction in middiastole".

Referring back to FIG. 1, the image reconstruction circuitry 36 reconstructs X-ray CT image data based on the projection data stored in the storage circuitry 35 under the control of the processing circuitry 37. Specifically, the image reconstruction circuitry 36 reconstructs X-ray CT image data individually from the projection data of a localizer image and projection data of an image for use in diagnosis under the reconstruction condition set by the processing circuitry 37. How the processing circuitry 37 determines the reconstruction condition will be described later.

Various reconstruction methods are available, including back projection, for example. Examples of the back projection include filtered back projection (FBP). Alternatively, the image reconstruction circuitry 36 can reconstruct X-ray CT image data by iterative reconstruction.

The image reconstruction circuitry 36 generates image data by performing various kinds of image processing to the X-ray CT image data. The image reconstruction circuitry 36 stores the reconstructed X-ray CT image data and the image data resulting from various kinds of image processing in the storage circuitry 35.

The processing circuitry 37 performs control over the X-ray CT apparatus 1 as a whole by controlling the operations of the gantry 10, the couch 20, and the console 30.

Specifically, the processing circuitry 37 causes the scan control circuitry 33 to control the gantry 10 to perform CT scans. The processing circuitry 37 causes the image reconstruction circuitry to control the console 30 to perform image reconstruction and image generation. The processing circuitry 37 also causes the display 32 to display various kinds of image data stored in the storage circuitry 35.

The electrocardiograph 40 is attached to the subject P to acquire electrocardiogram data from the subject P. The electrocardiograph 40 obtains electrocardiogram waveforms of the subject P from the electrocardiogram data. The electrocardiograph 40 transmits the electrocardiogram waveforms to the console 30. In the present embodiment, the electrocardiograph 40 transmits the electrocardiogram waveforms in real time. The console 30 stores the electrocardiogram waveforms in the storage circuitry 35 upon receipt from the electrocardiograph 40.

Namely, the storage circuitry 35 stores therein the electrocardiogram waveforms. Herein, a duration of one cycle of the electrocardiogram waveforms is normalized to zero to 100%, and each position in the duration represented by % is referred to as a cardiac phase. For example, in the cardiac phase, an indefinite duration from an R wave to the next R wave is normalized to zero to 100%.

The electrocardiograph 40 obtains analysis information by analyzing the electrocardiogram waveforms of the subject P and transmits it to the console 30. The console 30 receives and stores the analysis information from the electrocardiograph 40 in the storage circuitry 35. The electrocardiograph 40 may transmit the analysis information on the electrocardiogram waveforms at a timing later than the electrocardiogram waveforms. In this manner the electrocardiograph 40 can transmit the analysis information to the X-ray CT apparatus 1 even when it takes time for the analysis.

The analysis information includes diagnosis information and measurement information. The diagnosis information represents a clinical state of the subject. For example, the diagnosis information represents electrocardiographic findings of the subject P by the Minnesota code classification system, which is a coding system for expressing electrocardiographic findings in an objective and unified manner.

Examples of the diagnosis information include, but are not limited to, normal sinus rhythm, atrioventricular block, short PQ interval, pacemaker in operation, ventricular premature contraction, ventricular premature contraction (bigeminy), and atrial fibrillation.

The measurement information represents characteristics of biological information. The measurement information refers to, for example, information computable based on the electrocardiogram waveforms and representable by numerical values. Examples of the measurement information include, but are not limited to, PR (PQ) interval, RR interval, heart-rate variation, frequency of irregular pulse.

The overall structure and configuration of the X-ray CT apparatus 1 according to the present embodiment have been described above. With such features, the X-ray CT apparatus 1 of the present embodiment functions to obtain the analysis information as to the subject P and set a suitable examination condition based on the analysis information, depending on the clinical state of the subject P.

To implement such functions, the processing circuitry 37 executes a system control function 37*a*, a display control function 37*b*, a first obtaining function 37*c*, a second obtaining function 37*d*, and a setting function 37*e*, as illustrated in FIG. 1.

The processing and functions to be performed by the elements of the processing circuitry 37, i.e., the system control function 37*a*, the display control function 37*b*, first obtaining function 37*c*, second obtaining function 37*d*, and setting function 37*e* in FIG. 1 are, for example, stored in computer-executable program format in the storage circuitry 35.

The processing circuitry 37 serves as a processor that retrieves and executes the respective computer programs from the storage circuitry 35 to implement the functions corresponding to the computer programs. In other words, having retrieved the computer programs, the processing circuitry 37 includes the functions illustrated within the processing circuitry 37 of FIG. 1.

The system control function 37*a* controls the overall operation of the X-ray CT apparatus 1 in a unified manner. For example, the system control function 37*a* controls the scan control circuitry 33 to perform a scan of the subject P according to a scan condition set by the setting function 37*e* as described later. For another example, the system control function 37*a* controls the image reconstruction circuitry 36 to perform an image reconstruction process under a reconstruction condition set by the setting function 37*e*.

The display control function 37*b* performs display control to display various kinds of information on the display. For example, the display control function 37*b* causes the display 32 to display image data generated based on the X-ray CT image data by the image reconstruction circuitry 36. For another example, the display control function 37*b* causes the display 32 to display a graphical user interface (GUI) that allows the operator to input various kinds of instructions and settings via the input circuitry 31.

In addition, the display control function 37*b* may cause the display 32 to display information representing an examination condition for examining the subject P.

The first obtaining function 37*c* obtains the electrocardiogram waveforms of the subject P acquired by the electrocardiograph 40. The electrocardiograph 40 is one example of biological monitor. The electrocardiogram waveform is one example of biological information. As an example, the first obtaining function 37*c* obtains the electrocardiogram waveforms of the subject P as transmitted in real time from the electrocardiograph 40 to the console 30.

The second obtaining function 37*d* obtains the analysis information resulting from the analysis of the electrocardiogram waveforms of the subject P. As an example, the second obtaining function 37*d* obtains the diagnosis information and the measurement information as transmitted from the electrocardiograph 40 to the console 30. The diagnosis information represents electrocardiographic findings of the subject P by the Minnesota code classification system. The measurement information represents, for instance, heart rate, PR interval, RR interval, or frequency of irregular pulse. The diagnosis information and the measurement information are exemplary analysis information.

The setting function 37*e* sets an examination condition based on the electrocardiogram waveforms obtained by the first obtaining function 37*c* and the diagnosis information and measurement information obtained by the second obtaining function 37*d*.

For example, the setting function 37*e* identifies a scan condition and a reconstruction condition corresponding to the diagnosis information obtained by the second obtaining function 37*d*, with reference to the examination-condition database 351 in the storage circuitry 35. The setting function 37*e* sets the identified scan condition and reconstruction condition according to the measurement information obtained by the second obtaining function 37*d*. The following will describe an operation of the setting function 37*e*, referring to FIG. 3 to FIG. 6, as an example.

First, an example that the diagnosis information obtained by the second obtaining function 37*d* indicates "equal pulse (normal sinus rhythm) and heart rate of 65 bpm or less" is explained. In this case, the setting function 37*e* identifies a scan condition and a reconstruction condition associated with the diagnosis information "equal pulse (normal sinus rhythm) and heart rate of 65 bpm or less", referring to the examination-condition database 351 in the storage circuitry 35. In the example of FIG. 2, the setting function 37*e* identifies a scan condition "irradiate only in middiastole" and a reconstruction condition "reconstruct middiastole".

Next, the setting function 37*e* sets a scan condition based on "irradiate only in middiastole" based on the measurement information obtained by the second obtaining function 37*d*. Likewise, the setting function 37*e* sets a reconstruction condition based on "reconstruct middiastole". The following will describe an operation of the setting function 37*e* when the diagnosis information indicates "equal pulse (normal sinus rhythm) and heart rate of 65 bpm or less", referring to FIG. 3, as an example.

Figure 3:
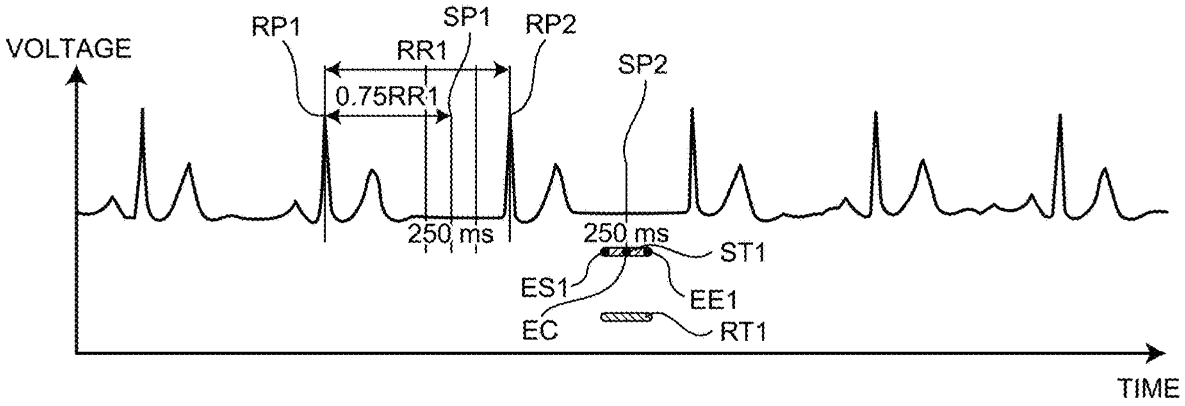
FIG. 3 is a graph for explaining one example of examination condition setting according to an embodiment.

FIG. 3 is a graph for explaining one example of examination condition setting. FIG. 3 depicts electrocardiogram waveforms of the subject P when the electrocardiographic findings indicate equal pulse (normal sinus rhythm) and a heart rate of 65 bpm or less. Point RP1 represents an R wave peak of the subject P for use in the scan condition setting. Point RP2 represents an R wave peak next the R wave peak RP1. Duration RR1 represents a length of time from the point RP1 to the point RP2 (RR interval).

In the example of FIG. 3, the setting function 37*e* identifies a time SP1 indicating 75% of the duration RR1 when the occurrence time of the point RP1 is defined as 0% and that of the point RP2 is defined as 100%. The time SP1 is close to the middle of middiastole.

The setting function 37*e* then predicts a time SP2 corresponding to the time SP1 in an RR interval following the duration RR1 on the premise that the RR intervals are uniform. The setting function 37*e* also determines an X-ray irradiation start time ES1 and an X-ray irradiation end time EE1 so that the time SP2 matches a time EC in the middle of an X-ray irradiation period and the subject P is irradiated with X-rays for the duration of 250 ms. In other words, the setting function 37*e* determines a scan timing ST1 included in the scan condition.

The setting function 37*e* sets an operation condition for the gantry 10 and the couch driver 21 to irradiate the subject P with X-rays at the set scan timing. In the present embodiment the operation condition is defined to be included in the scan condition.

The setting function 37*e* also sets a reconstruction timing RT1 included in the reconstruction condition to reconstruct image data of the subject P during the X-ray irradiation period under the set scan condition.

Next, an example that the diagnosis information obtained by the second obtaining function 37*d* represents "atrioventricular block" is described. In this case the setting function 37*e* identifies a scan condition and a reconstruction condition corresponding to the diagnosis information "atrioventricular block", referring to the examination-condition database 351 in the storage circuitry 35. In the example of FIG. 2, the setting function 37*e* identifies a scan condition "correct HR threshold according to PR interval . . . " and a reconstruction condition "reconstruct immediately prior to P wave based on PR-interval information".

The setting function 37*e* then sets a scan condition based on "correct HR threshold according to PR interval . . . " based on the measurement information obtained by the second obtaining function 37*d*. Likewise, the setting function 37*e* sets a reconstruction condition based on "reconstruct immediately prior to P wave based on PR-interval information". The following will describe an operation of the setting function 37*e* when the diagnosis information indicates "atrioventricular block", referring to FIG. 4, as an example.

Figure 4:
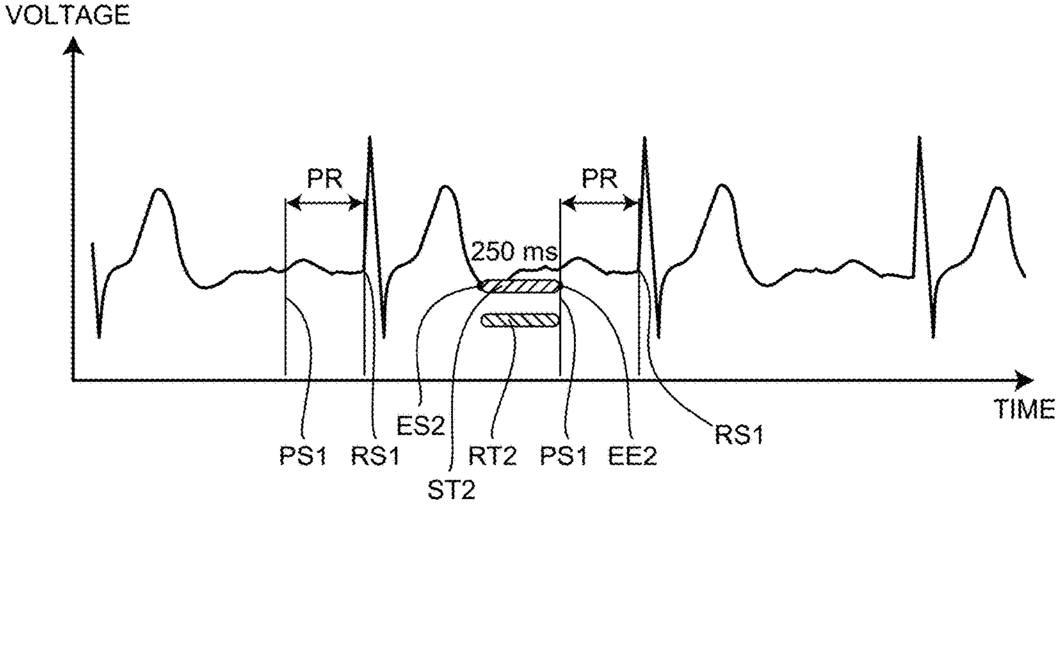
FIG. 4 is a graph for explaining another example of examination condition setting according to an embodiment.

FIG. 4 is a graph for explaining an example of examination condition setting. FIG. 4 depicts electrocardiogram waveforms of the subject P when the electrocardiographic findings indicate atrioventricular block. Point PS1 represents P wave rising of the subject P for use in the scan condition setting. Point RS1 represents R wave rising of the subject P for use in the scan condition setting. Duration PR represents a length of time from the point PS1 to the point RS1 (PR interval).

In the example of FIG. 4, the setting function 37*e* predicts a next P-wave rising time based on the duration PR. The setting function 37*e* sets a time immediately before (e.g., 5 ms before) the next P-wave rising time as an irradiation end time EE2. The setting function 37*e* sets a time 250 ms before the irradiation end time EE2 as an irradiation start time ES2. In other words, the setting function 37*e* sets a scan timing ST2. Alternatively, the setting function 37*e* may predict the next P-wave rising time from the PQ interval or RR interval.

The setting function 37*e* further sets a reconstruction timing RT2 to reconstruct image data of the subject P during the X-rays irradiation period under the set scan condition.

Next, an example that the diagnosis information obtained by the second obtaining function 37*d* indicates "atrial fibrillation" is described. In this case the setting function 37*e* identifies a scan condition and a reconstruction condition associated with the diagnosis information "atrial fibrillation", referring to the examination-condition database 351 in the storage circuitry 35. In the example of FIG. 2, the setting function 37*e* identifies a scan condition "prepare free area for data acquisition for several seconds . . . " and a reconstruction condition "reconstruct rear end of 250 ms data".

The setting function 37*e* then sets a scan condition based on "prepare free area for data acquisition for several seconds . . . " in accordance with the measurement information obtained by the second obtaining function 37*d*. Likewise, the setting function 37*e* sets a reconstruction condition based on "reconstruct rear end of 250 ms data". The following will describe an operation of the setting function 37*e* when the diagnosis information indicates "atrial fibrillation" referring to FIG. 5, as an example.

Figure 5:
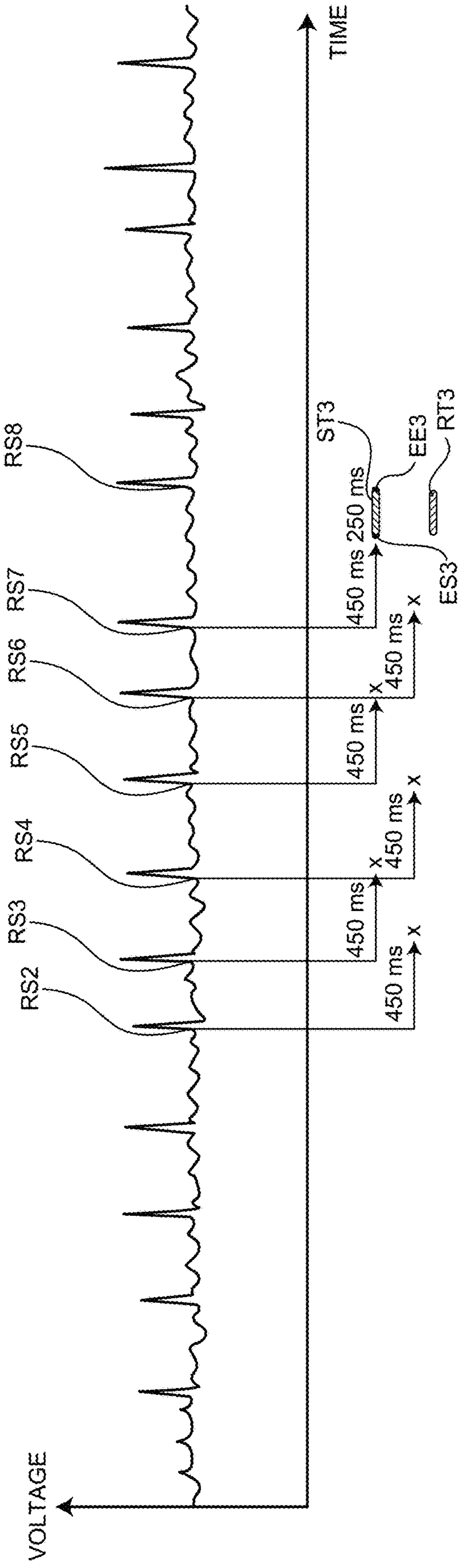
FIG. 5 is a graph for explaining another example of examination condition setting according to an embodiment.

FIG. 5 is a graph for explaining an example of examination condition setting. FIG. 5 depicts electrocardiogram waveforms of the subject P when the electrocardiographic findings indicate atrial fibrillation. Points RS2 to RS8 represent R wave risings for use in the scan condition setting.

In the example of FIG. 5, the setting function 37*e* detects R wave risings. Upon detecting an R wave rising, the setting function 37*e* starts counting the time. When detecting a next R wave rising before a lapse of 450 ms from the start of time counting, the setting function 37*e* resets the time count (indicated by "x" in FIG. 5). In FIG. 5 the setting function 37*e* resets the time count in the period from the points RS2 through RS6.

Upon detecting RS7 in FIG. 5, the setting function 37*e* sets a time count of 450 ms as an irradiation start time ES3. In this case, X-ray emission to the subject P is immediately started. Thus, when the electrocardiographic findings of the subject P indicate atrial fibrillation, the setting function 37*e* sets the operation condition for the gantry 10 and the couch driver 21 in advance in order to start X-ray irradiation at any moment.

The setting function 37*e* starts counting the time from the start of X-ray irradiation and sets a time count of 250 ms as an irradiation end time EE3. In other words, the setting function 37*e* sets a scan timing ST3. When detecting a next R wave before a lapse of 250 ms from the irradiation start time ES3, the system control function 37*a* discontinues the X-ray irradiation and the setting function 37*e* resets the time count from the start of X-ray irradiation.

If no next R wave is detected after a lapse of 250 ms, the system control function 37*a* may continue the X-ray irradiation for more than the period of 250 ms. In this case the setting function 37*e* may set the time at which a next R wave rising (RS8 in FIG. 5) is detected as the irradiation end time EE3.

The setting function 37*e* also sets a reconstruction timing RT3 to reconstruct image data of the subject P during the X-ray irradiation period according to the set scan condition. When the subject P has undergone the X-ray irradiation for more than 250 ms, the setting function 37*e* may determine, as the reconstruction timing, a period from a time 250 ms before the irradiation end time EE3 to the irradiation end time EE3.

Next, an example that the diagnosis information obtained by the second obtaining function 37*d* indicates "ventricular premature contraction (bigeminy)" is described. In this case the setting function 37*e* identifies a scan condition and a reconstruction condition associated with the diagnosis information "ventricular premature contraction (bigeminy)", referring to the examination-condition database 351 in the storage circuitry 35. In the example of FIG. 2, the setting function 37*e* identifies a scan condition "aim to scan second half of longer RR" and a reconstruction condition "reconstruct second half of longer RR".

The setting function 37*e* then sets a scan condition based on "aim to scan second half of longer RR" in accordance with the measurement information obtained by the second obtaining function 37*d*. Likewise, the setting function 37*e* sets a reconstruction condition based on "reconstruct second half of longer RR". The following will describe an operation of the setting function 37*e* when the diagnosis information indicates "ventricular premature contraction (bigeminy)", referring to FIG. 6, as an example.

Figure 6:
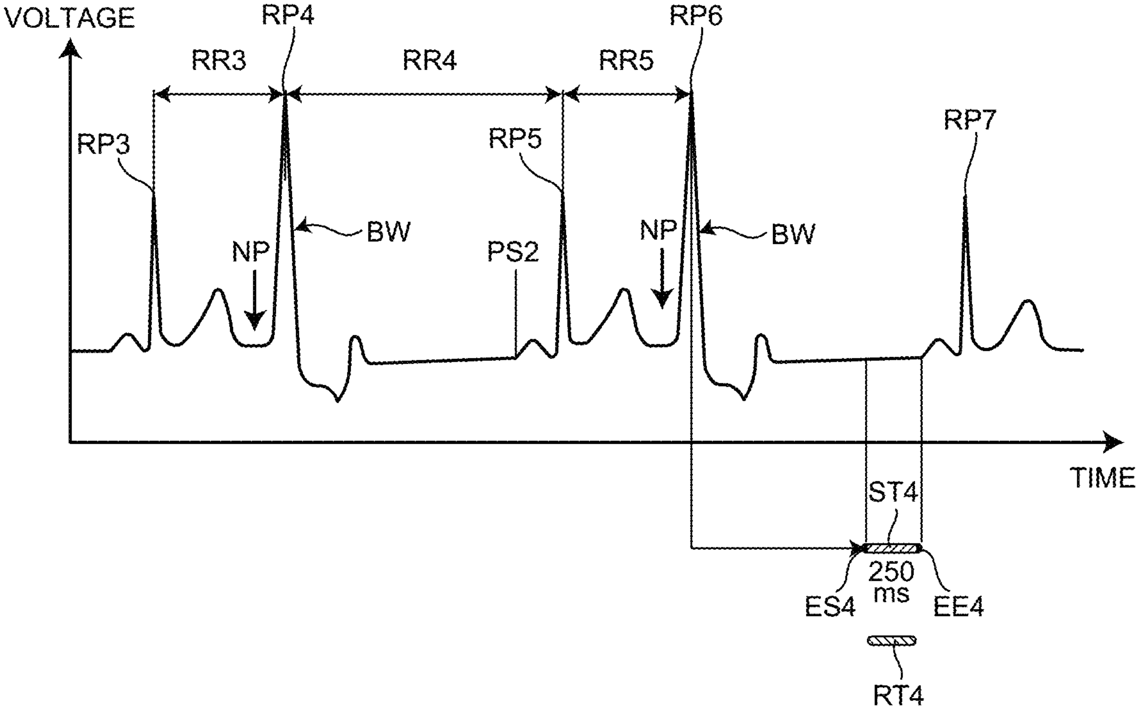
FIG. 6 is a graph for explaining another example of examination condition setting according to an embodiment.

FIG. 6 is a graph for explaining an example of examination condition setting. FIG. 6 depicts electrocardiogram waveforms of the subject P when the electrocardiographic findings indicate ventricular premature contraction (bigeminy). Point RP3 represents some R wave peak of the subject P. Point RP4 represents an R wave peak of the subject P for use in the scan condition setting. Point RP5 represents an R wave peak next the R wave peak RP4. Point RP6 represents an R wave peak next the R wave peak RP5.

Duration RR3 represents a length of time from the point RP3 to the point RP4 and a shorter RR interval. Duration RR4 represents a length of time from the point RP4 to the point RP5 and a longer RR interval. Duration RR5 represents a length of time from the point RP5 to the point RP6 and a shorter RR interval.

In the example of FIG. 6, the setting function 37*e* detects a finding NP and a finding BW from the waveform from the point RP3 to the point RP4. The finding NP represents disappearance of the P wave and the finding BW represents a wide QRS wave. After detecting the findings NP and BW, the setting function 37*e* detects a next P-wave rising PS2 from the waveform from the point RP4 to the point RP5.

Upon detecting the findings NP and BW from the waveform from the point RP5 to the point RP6, the setting function 37*e* sets a scan timing in a second half of the RR interval on the premise that an RR interval between the point RP6 and a next R-wave peak (expected point RP7) is equal to the duration RR4.

As an example, the setting function 37*e* starts counting the time from the time at which a peak of the wide QRS wave (point RP6 in FIG. 6) is detected. The setting function 37*e* determines the time at which a time count exceeds a predetermined time as an irradiation start time ES4. The predetermined time may be defined for each of subjects P based on a longer RR interval of the previous electrocardiogram from which bigeminy of the subject was detected.

The setting function 37*e* determines the time corresponding to the point PS2 as an irradiation end time EE4. The point PS2 is detected from the waveform from the point RP4 to the point RP5 in the RR interval between the point RP6 to the next R-wave peak. In other words, the setting function 37*e* sets a scan timing ST4. The setting function 37*e* also determines a duration from the time 250 ms before the irradiation end time EE4 to the irradiation end time EE4 as a reconstruction timing RT4. When the irradiation time is less than 250 ms, scanning of the subject P is iterated until a lapse of 250 ms.

The setting function 37*e* may predict a next P-wave rising time based on a longer RR interval of the previous electrocardiogram from which bigeminy of the subject P was detected, and set the predicted time as an irradiation end time and a time 250 ms before the irradiation end time as an irradiation start time. Further, when the measurement information includes the frequency of irregular pulse being less than a threshold, the setting function 37*e* may consider the subject P as having equal pulse and set a suitable examination condition for the subject P.

The above embodiments have described several examples of the examination condition setting for illustrative purpose, but it is not intended to limit the examination condition setting to such examples.

Figure 7:
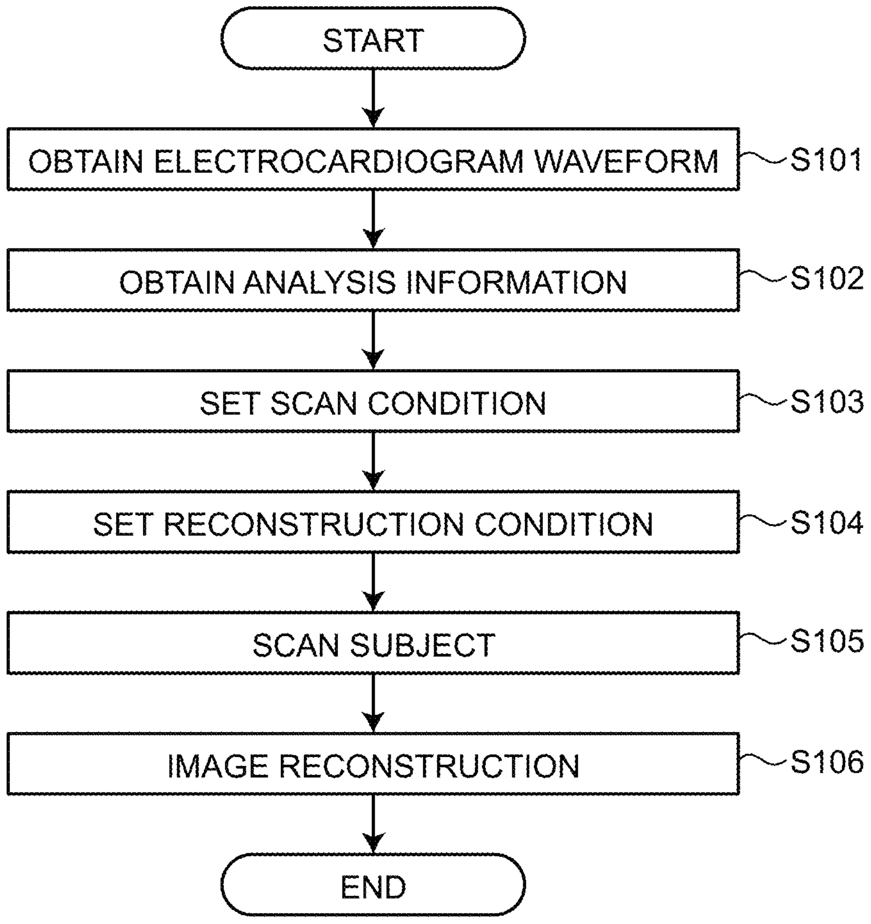
FIG. 7 is a flowchart illustrating exemplary processing to be performed by an X-ray CT apparatus according to an embodiment.

Now, processing to be performed by the X-ray CT apparatus 1 of one embodiment will be explained. FIG. 7 is a flowchart illustrating one example of processing to be performed by the X-ray CT apparatus 1 of one embodiment.

First, the first obtaining function 37*c* obtains electrocardiogram waveforms (step S101). For example, the first obtaining function 37*c* obtains electrocardiogram waveform data as transmitted from the electrocardiograph 40 in real time. The second obtaining function 37*d* then obtains analysis information (step S102). For example, the second obtaining function 37*d* obtains diagnosis information and measurement information resulting from analyzing the electrocardiogram waveforms transmitted from the electrocardiograph 40.

The setting function 37*e* sets a scan condition (step S103). For example, the setting function 37*e* identifies a scan condition associated with the diagnosis information obtained at step S102, with reference to the examination-condition database 351 in the storage circuitry 35. The setting function 37*e* also sets a scan timing and an operation condition for the respective elements of the X-ray CT apparatus 1 according to the scan condition, based on the measurement information obtained at step S102.

The setting function 37*e* sets a reconstruction condition (step S104). For example, the setting function 37*e* identifies a reconstruction condition associated with the diagnosis information obtained at step S102, with reference to the examination-condition database 351 in the storage circuitry 35. The setting function 37*e* also sets a reconstruction timing according to the reconstruction condition, based on the measurement information obtained at step S102.

Next, the system control function 37*a* controls the respective elements of the X-ray CT apparatus 1 to perform a scan of the subject P (step S105). For example, the system control function 37*a* controls the scan control circuitry 33 under the scan condition set at step S103. Under the control of the system control function 37*a*, the scan control circuitry 33 performs control over the operations of the gantry 10 and the couch driver 21 to irradiate the subject P with X-rays.

The system control function 37*a* reconstructs X-ray CT image data (step S106), completing the processing. For example, the system control function 37*a* controls the image reconstruction circuitry 36 according to the reconstruction condition set at step S104. The image reconstruction circuitry 36 reconstructs X-ray CT image data resulting from scanning the subject P at step S105, to generate image data.

The X-ray CT apparatus 1 according to the present embodiment described above obtains the electrocardiogram waveforms of the subject P acquired by the electrocardiograph 40, obtains the analysis information resulting from analyzing the electrocardiogram waveforms, and sets an examination condition based on the electrocardiogram waveforms and the analysis information.

In this manner, for example, the X-ray CT apparatus 1 can automatically set the scan condition and the reconstruction condition in accordance with the diagnosis information by simply obtaining the electrocardiogram waveforms, the measurement information, and the diagnosis information. In addition, the diagnosis information reflects the clinical state of the subject P. Namely, the X-ray CT apparatus 1 of one embodiment can set the scan condition and the reconstruction condition depending on the clinical state of the subject P. As such, the X-ray CT apparatus 1 can allow healthcare professionals such as a radiology technician to easily set a suitable scan condition and reconstruction condition for X-ray CT examination of the subject P depending on the clinical state of the subject P even if they are not familiar with clinical states related to the circulatory organs.

In addition, the X-ray CT apparatus 1 of the present embodiment may obtain the analysis information with a delay from the obtainment of the electrocardiogram waveforms. For example, the diagnosis information and the measurement information included in the analysis information are unlikely to largely change in a short period of time. Thus, the examination condition setting based on the analysis information is feasible even with a delay in obtaining the analysis information.

The above-described embodiments are implementable in modified form by partly changing the elements or functions of the X-ray CT apparatus 1, when appropriate. In this regard, exemplary modifications of the embodiments are presented below. The following will mainly describe different features from the embodiments and omit describing the same or similar features in detail. The modifications presented below may be implemented individually or in combination when appropriate.

First Modification

The above embodiments have described an example that the X-ray CT apparatus 1 obtains diagnosis information and measurement information from the electrocardiograph 40. In a first modification the X-ray CT apparatus 1 analyzes electrocardiogram waveforms by itself to obtain diagnosis information and measurement information.

According to the first modification, the second obtaining function 37*d* obtains analysis information based on the electrocardiogram waveforms obtained by the first obtaining function 37*c*. For example, the second obtaining function 37*d* analyzes the electrocardiogram waveforms obtained by the first obtaining function 37*c* to obtain diagnosis information and measurement information. The second obtaining function 37*d* may obtain either of the diagnosis information and the measurement information. The means to analyze the electrocardiogram waveforms is not limited to a particular means and any of a variety of known analyzing techniques is adoptable.

According to the first modification, the electrocardiograph 40 performs no analysis of electrocardiogram waveforms. This can lead to simplifying the electrocardiograph 40 in structure and configuration in the first modification.

Second Modification

The first modification has described an example that the X-ray CT apparatus 1 analyzes the electrocardiogram waveforms. In a second modification, for example, the analysis information is obtained from an exterior apparatus.

According to the second modification, the second obtaining function 37*d* obtains analysis information from an exterior apparatus. For instance, the second obtaining function 37*d* obtains diagnosis information and measurement information as a result of the most recent electrocardiographic test from a server such as an electronic medical record server. As an example, in response to an operator's instruction to obtain diagnosis information and measurement information via the input circuitry 31 of the console 30, the second obtaining function 37*d* obtains diagnosis information and measurement information as a result of the most recent electrocardiographic test.

Alternatively, the second obtaining function 37*d* may obtain analysis information directly input via the console 30. For example, the analysis information may be recorded on a computer-readable recording medium such as a flexible disk (FD), a CD-ROM, a magneto-optical disk (MOD), or a digital versatile disk (DVD). In such a case the second obtaining function 37*d* may read and obtain analysis information from the recording medium using a recording-medium reader (not illustrated) connected to the console 30.

In the second modification, the second obtaining function 37*d* of the X-ray CT apparatus 1 no longer performs the analysis process. Thus, the second modification makes it possible to lessen the processing load on the processing circuitry 37 of the X-ray CT apparatus 1.

Third Modification

In the embodiments and modifications as above, the biological monitor is exemplified by the electrocardiograph. The biological monitor is not limited to the electrocardiograph and may be, for example, a respiration detector 50.

Figure 8:
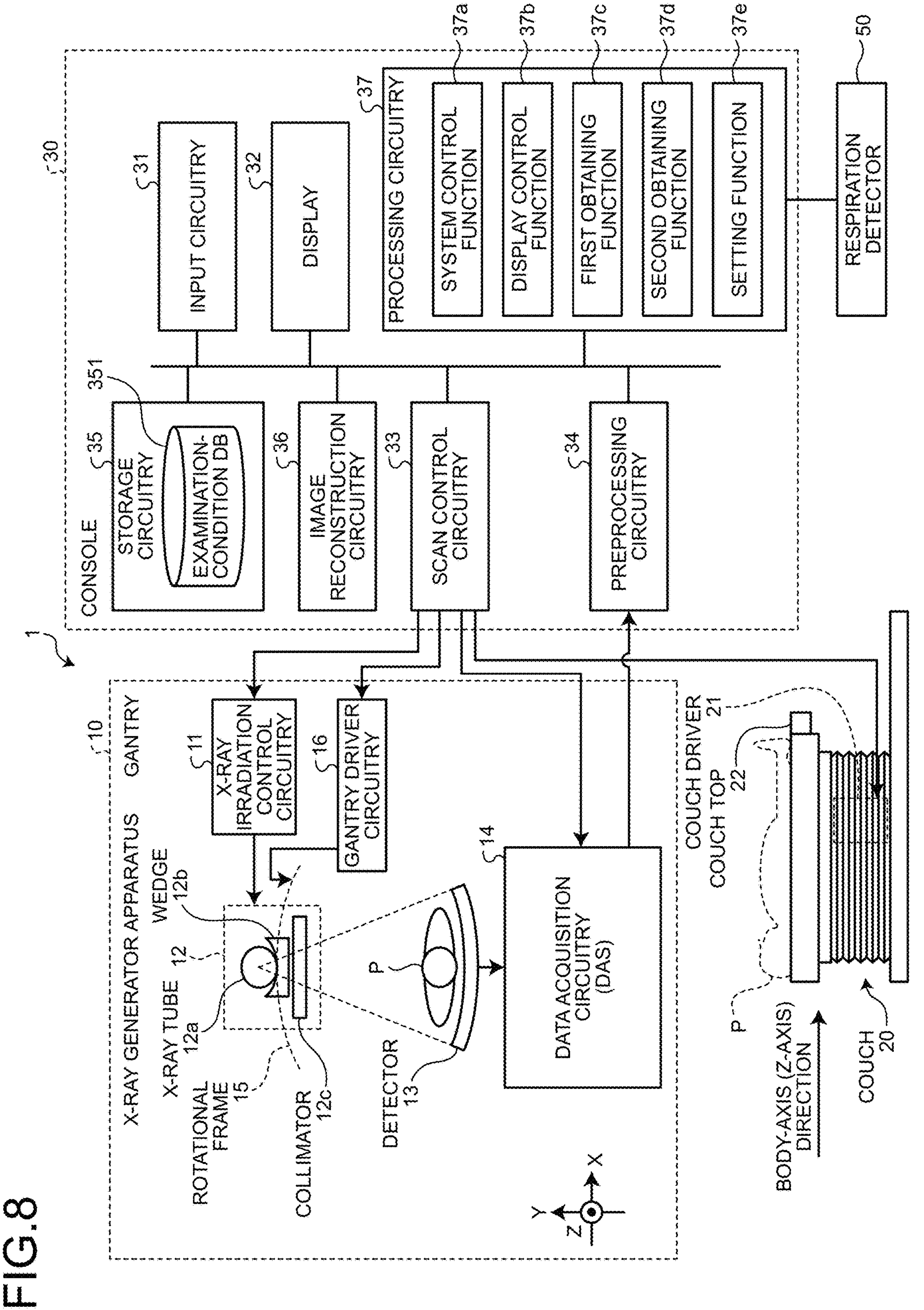
FIG. 8 illustrates an exemplary configuration of an X-ray CT apparatus according to a third modification.

FIG. 8 is a schematic block diagram illustrating an exemplary configuration of an X-ray CT apparatus according to a third modification. In the third modification, the X-ray CT apparatus 1 is connected to the respiration detector 50.

The respiration detector 50 includes a respiration sensor to obtain respiratory waveforms of the subject P. The respiration sensor includes, for example, a laser generator and a light receiver. The respiration sensor processes a reflected optical signal by the abdominal surface of the subject P to obtain a length of time from laser irradiation to reception of reflected light or phase variations in the reflected optical signal. The respiration sensor iteratively computes the distance between the laser generator and the abdominal surface of the subject P in real time based on the time or phase variations.

In the third modification the respiration detector 50 includes a laser generator and a light receiver by way of example, however, the respiration detector 50 is not limited to such an example. As an example, the respiration detector 50 may include a band and a pressure sensor. The band is attached to the abdominal region of the subject P and the pressure sensor is attached to a location in-between the band and the abdominal region to observe a respiratory state of the subject P from variations in pressure. For another example, the respiration detector 50 may include an optical reflective member and a camera. The optical reflective member may be attached to a material placed on the abdominal region and be captured by the camera, to observe a respiratory state of the subject P by tracking the motion of the optical reflective member.

The respiration detector 50 obtains and transmits the respiratory waveforms to the console 30. The console 30 stores the respiratory waveforms in the storage circuitry 35 upon receipt. Thus, the storage circuitry 35 stores therein the respiratory waveforms. A duration of one cycle of respiratory waveforms is normalized to zero to 100%, and each position in the duration represented by % is referred to as a respiratory phase. For example, in the respiratory phase, a duration from a maximal inspiration to a next maximal inspiration is normalized to zero to 100%.

Further, the respiration detector 50 obtains analysis information by analyzing the respiratory waveforms of the subject P and transmits it to the console 30. The console 30 stores the analysis information in the storage circuitry 35 upon receipt from the respiration detector 50.

According to the third modification, the scan control circuitry 33 performs respiratory-gated scanning under the control of the system control function 37*a* of the processing circuitry 37. The respiratory-gated scanning refers to performing scanning in a duration of a maximal inspiration being the peak of a respiratory waveform or a maximal expiration being the bottom of a respiratory waveform.

According to the third modification, the first obtaining function 37*c* of the processing circuitry 37 obtains respiratory waveforms of the subject P acquired by the respiration detector 50. For example, the first obtaining function 37*c* obtains respiratory waveforms of the subject P, as transmitted from the respiration detector 50 to the console 30 in real time.

The second obtaining function **37*d* obtains analysis information resulting from analyzing the respiratory waveforms of the subject P. For example, the second obtaining function 37*d* obtains measurement information representing a respiratory cycle, as transmitted from the respiration detector 50 to the console 30**.

The setting function **37*e* sets an examination condition based on the respiratory waveforms obtained by the first obtaining function 37*c* and the measurement information obtained by the second obtaining function 37*d***.

Although not shown, the examination-condition database 351 in the storage circuitry 35 of the third modification contains respiratory cycle, delay time from a start of contrast injection to a scan start, scan time, and reconstruction timing in association with one another. The delay time and the scan time are examples of scan condition.

For example, the delay time and the scan time are associated with the respiratory cycle so as to allow scanning of the subject P to start and end at appropriate timing in the end-tidal phase in which the motion of the subject P diminishes. The reconstruction timing is associated with the respiratory cycle so as to reconstruct image data during a suitable duration in the end-tidal phase in which the motion of the subject P diminishes, for example.

For example, the setting function **37*e* identifies a delay time and a scan time associated with the respiratory cycle obtained by the second obtaining function 37*d*, referring to the examination-condition database 351. The setting function 37*e* sets a scan condition in accordance with the identified delay time and scan time. The setting function 37*e* further sets a reconstruction timing corresponding to the respiratory cycle obtained by the second obtaining function 37*d*, with reference to the examination-condition database 351**.

In the third modification the X-ray CT apparatus 1 is connected to only the respiration detector 50, however, it may be connected to the respiration detector 50 and another biological monitor such as the electrocardiograph 40.

According to the third modification it is possible for the operator to set examination conditions of the X-ray CT apparatus 1 based on the analysis information obtained by analyzing the biological information from various biological monitors.

Fourth Modification

The embodiments and modifications have described the X-ray CT apparatus 1 as an example of image diagnosis apparatus but are not intended to limit the image diagnosis apparatus to the X-ray CT apparatus 1. Other examples of the image diagnosis apparatus include an image diagnosis apparatus for the circulatory organs (X-ray angiography apparatus) and a magnetic resonance imaging (MRI) apparatus.

For example, the MRI apparatus as the image diagnosis apparatus sets an imaging condition for ECG gated imaging based on the analysis information as to the electrocardiogram waveforms. In ECG gated imaging, MRI signals are acquired in synchronization with electrocardiogram waveforms.

According to the fourth modification, it is possible to allow the operator to easily set suitable examination conditions of various kinds of image diagnosis apparatuses according to the analysis information provided by the biological monitor.

The term "processor" used herein signifies circuitry such as a central processing unit (CPU), a graphics processing unit (GPU), an application specific integrated circuit (ASIC), a simple programmable logic device (SPLD), a complex programmable logic device (CPLD), or a field programmable gate array (FPGA).

The processor can implement functions by retrieving and executing computer programs from storage circuitry. In place of being stored in the storage circuitry, the computer programs may be directly embedded in the circuitry of the processor. In this case the processor implements functions by retrieving and executing computer programs from its circuitry.

According to the embodiments, processors can be individually constituted as a single piece of circuitry, or a single processor can be constituted of a combination of multiple independent circuits to implement the respective functions. Alternatively, the elements shown in FIG. 1 may be integrated into a single processor to implement the respective functions.

The respective elements of the apparatuses and devices depicted in the figures of the above embodiments represent functional concepts and may not be physically structured as depicted. Namely, part or all of the apparatuses and devices can be distributed or integrated in any functional or physical unit depending on various loads or usage, in addition to the configurations shown in the figures.

The processing and functions performed by each of the apparatuses and devices can be entirely or partially implemented by a CPU or computer programs read and executed by the CPU or can be implemented as hardware by wired logic.

The control methods described in the embodiments can be implemented by execution of a prepared control program using a computer such as a personal computer or a workstation. Such a control program can be distributed via a network such as the Internet.

The control program can be recorded on a computer-readable recording medium such as a hard disk, FD, CD-ROM, MOD, or DVD and can be retrieved and executed from the recording medium by a computer.

According to at least one of the embodiments described above, it is made possible to easily set suitable examination conditions according to the analysis information provided from the biological monitor.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus comprising processing circuitry configured to:

obtain biological information about a subject acquired by a biological monitor;

obtain analysis information resulting from analysis of the obtained biological information; and set an examination condition for capturing an image of the subject by a scan, based on the obtained biological information and the obtained analysis information, wherein the biological monitor includes an electrocardiograph, and the processing circuitry is configured to obtain an electrocardiogram waveform of the subject in real time as transmitted from the electrocardiograph;

the obtained analysis information including diagnosis information representing a clinical state of the subject and measurement information representing a characteristic of the obtained biological information, the diagnosis information including an electrocardiographic finding representing a finding of the electrocardiogram waveform of the subject, the electrocardiographic finding including at least one of an equal pulse, ventricular premature contraction, atrioventricular block, short PQ interval, pacemaker in operation, bigeminy, or atrial fibrillation, identify a method of setting the examination condition corresponding to the diagnosis information included in the obtained analysis information from the diagnosis information included in the obtained analysis information and an examination-condition database (DB) including a plurality of sets of pieces of diagnosis information and methods of setting examination conditions, and set the examination condition based on the identified method of setting the examination condition and the measurement information, wherein the examination condition includes a scan condition and a reconstruction condition, the scan condition including a scan timing representing a temporal condition for scanning the subject and an operation condition for elements of the medical image diagnosis apparatus to scan the subject at the scan timing, and the reconstruction condition including a reconstruction timing representing a temporal condition for reconstructing medical image data of the subject that is obtained by scanning the subject, when the diagnosis information included in the obtained analysis information indicates the equal pulse, the setting the examination condition includes setting, based on the identified method of setting the examination condition and the measurement information, a condition corresponding to irradiation only during middiastole as the scan condition and a condition corresponding to reconstruction in middiastole as the reconstruction condition, when the diagnosis information included in the obtained analysis information indicates the atrioventricular block, the setting the examination condition includes setting, based on the identified method of setting the examination condition and the measurement information, a condition corresponding to correcting HR threshold according to PR interval as the scan condition and a condition corresponding to reconstructing immediately prior to P wave based on PR-interval information as the reconstruction condition, when the diagnosis information included in the obtained analysis information indicates the atrial fibrillation, the setting the examination condition includes setting, based on the identified method of setting the examination condition and the measurement information, a condition corresponding to preparing free area for data acquisition for several seconds as the scan condition and a condition corresponding to reconstructing, within a duration of 250 milliseconds or longer starting 450 milliseconds after an R-wave rising and ending at a next R-wave rising, a section of 250 milliseconds having a front end 250 millisecond before the end of the duration and a rear end at the end of the duration as the reconstruction condition, and when the diagnosis information included in the obtained analysis information indicates the bigeminy, the setting the examination condition includes setting, based on the identified method of setting the examination condition and the measurement information, a condition corresponding to aiming to scan second half of longer RR as the scan condition and a condition corresponding to reconstructing the second half of longer RR as the reconstruction condition, control, based on the scan condition set, the medical image diagnosis apparatus to execute capturing the image of the subject by the scan, and control, based on the reconstruction condition set, the medical image diagnosis apparatus to perform an image generation process.

2. The medical image diagnosis apparatus according to claim 1, wherein the processing circuitry is configured to obtain the analysis information with a delay from obtaining the biological information.

3. The medical image diagnosis apparatus according to claim 1, wherein the measurement information includes at least one of PR interval, PQ interval, RR interval, heart-rate variation, or frequency of irregular pulse.

4. An X-ray computed tomography apparatus, comprising:

a gantry that rotationally moves an X-ray tube;

a couch having a couch top on which a subject is to be laid; and processing circuitry configured to obtain biological information about the subject acquired by a biological monitor, obtain analysis information resulting from analysis of the obtained biological information, set an examination condition for capturing an image of the subject by a scan, based on the obtained biological information and the obtained analysis information, and control operations of the gantry and the couch to irradiate the subject with an X-ray under the set examination condition, wherein the biological monitor includes an electrocardiograph, and the processing circuitry is configured to obtain an electrocardiogram waveform of the subject in real time as transmitted from the electrocardiograph;

the obtained analysis information including diagnosis information representing a clinical state of the subject and measurement information representing a characteristic of the obtained biological information, the diagnosis information including an electrocardiographic finding representing a finding of the electrocardiogram waveform of the subject, the electrocardiographic finding including at least one of an equal pulse, ventricular premature contraction, atrioventricular block, short PQ interval, pacemaker in operation, bigeminy, or atrial fibrillation, identify a method of setting the examination condition corresponding to the diagnosis information included in the obtained analysis information from the diagnosis information included in the obtained analysis information and an examination-condition database (DB) including a plurality of sets of pieces of diagnosis information and methods of setting examination conditions, and set the examination condition based on the identified method of setting the examination condition and the measurement information, wherein the examination condition includes a scan condition and a reconstruction condition, the scan condition including a scan timing representing a temporal condition for scanning the subject and an operation condition for elements of the medical image diagnosis apparatus to scan the subject at the scan timing, and the reconstruction condition including a reconstruction timing representing a temporal condition for reconstructing medical image data of the subject that is obtained by scanning the subject, when the diagnosis information included in the obtained analysis information indicates the equal pulse, the setting the examination condition includes setting, based on the identified method of setting the examination condition and the measurement information, a condition corresponding to irradiation only during middiastole as the scan condition and a condition corresponding to reconstruction in middiastole as the reconstruction condition, when the diagnosis information included in the obtained analysis information indicates the atrioventricular block, the setting the examination condition includes setting, based on the identified method of setting the examination condition and the measurement information, a condition corresponding to correcting HR threshold according to PR interval as the scan condition and a condition corresponding to reconstructing immediately prior to P wave based on PR-interval information as the reconstruction condition, when the diagnosis information included in the obtained analysis information indicates the atrial fibrillation, the setting the examination condition includes setting, based on the identified method of setting the examination condition and the measurement information, a condition corresponding to preparing free area for data acquisition for several seconds as the scan condition and a condition corresponding to reconstructing, within a duration of 250 milliseconds or longer starting 450 milliseconds after an R-wave rising and ending at a next R-wave rising, a section of 250 milliseconds having a front end 250 millisecond before the end of the duration and a rear end at the end of the duration as the reconstruction condition, and when the diagnosis information included in the obtained analysis information indicates the bigeminy, the setting the examination condition includes setting, based on the identified method of setting the examination condition and the measurement information, a condition corresponding to aiming to scan second half of longer RR as the scan condition and a condition corresponding to reconstructing the second half of longer RR as the reconstruction condition, control, based on the scan condition set, the medical image diagnosis apparatus to execute capturing the image of the subject by the scan, and control, based on the reconstruction condition set, the medical image diagnosis apparatus to perform an image generation process.

5. A medical image diagnosis system comprising:

a biological monitor including processing circuitry configured to acquire biological information about a subject, and output the biological information; and a medical image diagnosis apparatus including processing circuitry configured to obtain the biological information from the biological monitor, obtain analysis information resulting from analysis of the obtained biological information, set an examination condition for capturing an image of the subject by a scan, based on the obtained biological information and the obtained analysis information, wherein the biological monitor includes an electrocardiograph, and the processing circuitry of the medical image diagnosis is configured to obtain an electrocardiogram waveform of the subject in real time as transmitted from the electrocardiograph;

the obtained analysis information including diagnosis information representing a clinical state of the subject and measurement information representing a characteristic of the obtained biological information, the diagnosis information including an electrocardiographic finding representing a finding of the electrocardiogram waveform of the subject, the electrocardiographic finding including at least one of an equal pulse, ventricular premature contraction, atrioventricular block, short PQ interval, pacemaker in operation, bigeminy, or atrial fibrillation, identify a method of setting the examination condition corresponding to the diagnosis information included in the obtained analysis information from the diagnosis information included in the obtained analysis information and an examination-condition database (DB) including a plurality of sets of pieces of diagnosis information and methods of setting examination conditions, and set the examination condition based on the identified method of setting the examination condition and the measurement information, wherein the examination condition includes a scan condition and a reconstruction condition, the scan condition including a scan timing representing a temporal condition for scanning the subject and an operation condition for elements of the medical image diagnosis apparatus to scan the subject at the scan timing, and the reconstruction condition including a reconstruction timing representing a temporal condition for reconstructing medical image data of the subject that is obtained by scanning the subject, when the diagnosis information included in the obtained analysis information indicates the equal pulse, the setting the examination condition includes setting, based on the identified method of setting the examination condition and the measurement information, a condition corresponding to irradiation only during middiastole as the scan condition and a condition corresponding to reconstruction in middiastole as the reconstruction condition, when the diagnosis information included in the obtained analysis information indicates the atrioventricular block, the setting the examination condition includes setting, based on the identified method of setting the examination condition and the measurement information, a condition corresponding to correcting HR threshold according to PR interval as the scan condition and a condition corresponding to reconstructing immediately prior to P wave based on PR-interval information as the reconstruction condition, when the diagnosis information included in the obtained analysis information indicates the atrial fibrillation, the setting the examination condition includes setting, based on the identified method of setting the examination condition and the measurement information, a condition corresponding to preparing free area for data acquisition for several seconds as the scan condition and a condition corresponding to reconstructing, within a duration of 250 milliseconds or longer starting 450 milliseconds after an R-wave rising and ending at a next R-wave rising, a section of 250 milliseconds having a front end 250 millisecond before the end of the duration and a rear end at the end of the duration as the reconstruction condition, and when the diagnosis information included in the obtained analysis information indicates the bigeminy, the setting the examination condition includes setting, based on the identified method of setting the examination condition and the measurement information, a condition corresponding to aiming to scan second half of longer RR as the scan condition and a condition corresponding to reconstructing the second half of longer RR as the reconstruction condition, control, based on the scan condition set, the medical image diagnosis apparatus to execute capturing the image of the subject by the scan, and control, based on the reconstruction condition set, the medical image diagnosis apparatus to perform an image generation process.

* * * * *